US009456754B2

(12) United States Patent
Kocherscheidt et al.

(10) Patent No.: US 9,456,754 B2
(45) Date of Patent: Oct. 4, 2016

(54) METHOD FOR RECORDING MULTIPLE THREE-DIMENSIONAL IMAGES OF A DENTAL OBJECT

(75) Inventors: Gerrit Kocherscheidt, Walldorf (DE); Anders Adamson, Darmstadt (DE); Björn Popilka, Hemsbach (DE); Frank Thiel, Ober-Ramstadt (DE)

(73) Assignee: Sirona Dental Systems GmbH, Bensheim (DE)

( * ) Notice: Subject to any disclaimer, the term of this patent is extended or adjusted under 35 U.S.C. 154(b) by 196 days.

(21) Appl. No.: 14/236,517

(22) PCT Filed: Aug. 1, 2012

(86) PCT No.: PCT/EP2012/065011
§ 371 (c)(1),
(2), (4) Date: Jan. 31, 2014

(87) PCT Pub. No.: WO2013/017617
PCT Pub. Date: Feb. 7, 2013

(65) Prior Publication Data
US 2014/0177931 A1    Jun. 26, 2014

(30) Foreign Application Priority Data
Aug. 1, 2011    (DE) .................. 10 2011 080 180

(51) Int. Cl.
*G06K 9/00* (2006.01)
*A61B 5/00* (2006.01)
(Continued)

(52) U.S. Cl.
CPC ........... *A61B 5/0088* (2013.01); *A61B 5/0068* (2013.01); *A61C 9/0046* (2013.01);
(Continued)

(58) Field of Classification Search
None
See application file for complete search history.

(56) References Cited

U.S. PATENT DOCUMENTS 5,471,987 A * 12/1995 Nakazawa ............... G06T 5/20
128/925
5,525,808 A * 6/1996 Irie ....................... G03F 9/7003
250/548
(Continued)

FOREIGN PATENT DOCUMENTS

EP    1 607 041 B1    1/2008
EP    1 607 064 B1    9/2008
(Continued)

OTHER PUBLICATIONS

W. Jacquet et al., "2D image registration using focused mutual information for application in dentistry", Computers in Biology and Medicine, vol. 39, No. 6 (2009) 545-53.
(Continued)

*Primary Examiner* — Wenpeng Chen
(74) *Attorney, Agent, or Firm* — Fitzpatrick, Cella, Harper & Scinto

(57) ABSTRACT

A method and apparatus for forming an overall image of an object from a plurality of images. Each image includes three-dimensional data and color data and is segmented based on the color data to identify a first region with hard tissue and a second region with soft tissue. For each image, first and second weighting factors may be assigned. Points in the second region with a larger distance to a corresponding proximate part of the first region may have a smaller second weighting factor than a point with a smaller distance to a corresponding proximate part of the first region. The second weighting factor may be variable, with its value dependent upon a value of a first area section corresponding to the first region.

24 Claims, 2 Drawing Sheets

(51) Int. Cl.
*G06T 7/00* (2006.01)
*A61C 9/00* (2006.01)

(52) U.S. Cl.
CPC ........... *G06T7/0012* (2013.01); *G06T 7/0028* (2013.01); *A61B 5/0064* (2013.01); *A61C 9/006* (2013.01); *G06T 2207/10024* (2013.01); *G06T 2207/10028* (2013.01); *G06T 2207/30036* (2013.01)

(56) References Cited

U.S. PATENT DOCUMENTS

| | | | | |
|---|---|---|---|---|
| 5,960,102 | A * | 9/1999 | Van Eeuwijk | A61B 6/5252 378/160 |
| 6,014,473 | A * | 1/2000 | Hossack | A61B 8/145 348/169 |
| 6,985,638 | B1 * | 1/2006 | Aoki | H04N 5/2624 345/645 |
| 7,080,979 | B2 | 7/2006 | Rubbert et al. | |
| 7,319,529 | B2 | 1/2008 | Babayoff | |
| 7,511,829 | B2 | 3/2009 | Babayoff | |
| 7,698,068 | B2 * | 4/2010 | Babayoff | A61B 1/00009 433/37 |
| 7,724,378 | B2 | 5/2010 | Babayoff | |
| 8,358,876 | B1 * | 1/2013 | Gilra | G06T 3/0012 345/418 |
| 2001/0017945 | A1 * | 8/2001 | Horie | H04N 1/3876 382/284 |
| 2005/0018901 | A1 * | 1/2005 | Kaufmann | G06T 17/20 382/154 |
| 2005/0019732 | A1 * | 1/2005 | Kaufmann | A61C 7/00 433/213 |
| 2005/0283065 | A1 * | 12/2005 | Babayoff | A61B 1/00009 600/407 |
| 2008/0172386 | A1 * | 7/2008 | Ammar | G06F 19/3443 |
| 2008/0175509 | A1 * | 7/2008 | Wheeler | G06T 7/0028 382/260 |
| 2008/0232714 | A1 | 9/2008 | Nord et al. | |
| 2009/0060373 | A1 * | 3/2009 | Perera | G06T 7/20 382/264 |
| 2009/0175555 | A1 * | 7/2009 | Mahowald | H04N 5/23232 382/274 |
| 2009/0231649 | A1 | 9/2009 | Sirat | |
| 2010/0303341 | A1 | 12/2010 | Häusler | |
| 2011/0026671 | A1 * | 2/2011 | Shi | A61B 6/14 378/39 |

FOREIGN PATENT DOCUMENTS

| | | | | |
|---|---|---|---|---|
| JP | | 10005229 A * | 1/1998 | |
| JP | WO | 2008126560 A1 * | 10/2008 | ............ A61C 5/08 |
| WO | | 2009063087 A2 | 5/2009 | |

OTHER PUBLICATIONS

A.E. Johnson et al., "Registration and integration of textured 3D data", Image and Vision Computing, vol. 17, No. 2 (1999) 135-47.

* cited by examiner

METHOD FOR RECORDING MULTIPLE THREE-DIMENSIONAL IMAGES OF A DENTAL OBJECT

CROSS REFERENCE TO RELATED APPLICATIONS

The present application is a §371 of PCT/EP2012/065011 filed Aug. 1, 2012 and claims benefit under 35 U.S.C. §119(a)-(d) of German Application No. 10 2011 080 180.4 filed Aug. 1, 2011. Each of those applications is hereby incorporated by reference as if set forth fully herein.

TECHNICAL FIELD

The invention relates to a method for recording multiple three-dimensional images of a dental object, wherein each of the three-dimensional images comprises 3D measured data and color data of a measured surface of the object, wherein the individual images are combined into an overall image using a computer-assisted recording algorithm.

PRIOR ART

Several methods for recording three-dimensional images are known from the prior art for assembling these individual images into an overall image.

Recording is necessary when the object to be recorded is detected not with a single image but instead only with multiple images. This is necessary, for example, in the case of dental objects that are rather large, such as multi-component bridges, or in the case of teeth which must be recorded from all sides.

U.S. Pat. No. 7,698,068 B2 discloses a method for recording overlapping regions. In the first step, the data records are separated into a first tissue data record for hard tissue and a second tissue data record for soft tissue, based on the different color properties. In a second step, the data records are merged based on the overlapping regions of the first tissue data record for hard tissue. The second tissue data records for soft tissue are thus omitted from the recording. The quality of the overall image that has been formed by merging the individual images is therefore improved. The individual images comprise 3D image data and color data generated in a confocal measurement of the dental object.

One disadvantage of this method is that regions with soft tissue are completely omitted and only regions with hard tissue are used for the recording. Therefore, in particular when the regions with hard tissue are small, recording errors can result in a defective overlapping of the individual images and thus to a defective overall image.

The object of the present invention is therefore to provide a method for recording multiple three-dimensional images of a dental object, which will permit recording that is as free of errors as possible.

SUMMARY OF THE INVENTION

One subject matter of the invention is a method for recording multiple three-dimensional images of a dental object. Each of the three-dimensional images comprises 3D measured data and color data of a measured surface of the object. Using a computer-assisted recording algorithm, the individual images are compiled into an overall image, wherein first regions with hard tissue and second regions with soft tissue are identified in each of the images using a segmentation method, which depends on the color data. When using the recording algorithm, the first regions and the second regions are weighted with different weighting factors.

In digital acquisition of dental objects, in particular for CAD/CAM system, multiple images of the dental object are made from different directions. The individual images are combined using the recording algorithm to form an overall image. Corresponding structures in the individual images are recognized and superimposed in this process. Conventional automated structure recognition methods are used for recognition of the corresponding structures.

The individual images may be generated using any three-dimensional imaging process such as a strip projection method or a confocal imaging method. In a confocal imaging method using a broadband spectrum, the 3D measured data reproducing the three-dimensional structure of the dental object, and the color data reproducing the actual color of the object surface, are determined at the same time by analyzing the beam of light reflected by the object by using a confocal optical arrangement and a color sensor.

In a strip projection method, the measured object is illuminated with a pattern of parallel light and dark strips or even colored strips. These strips are formed by projecting an optically structured element, e.g., a slide or a digital light modulator (DLM) into the measured volume. In another step, a digital camera is used to record the projected strip pattern at a known viewing angle relative to the projection. In the analysis, the sensor position of a strip transition on the camera sensor is allocated to precisely one projected strip on the optically structured element. By using a previously known pinhole camera model for the observation beam path and the projection beam path, the distance of the illuminated object from a previously defined origin can be determined from the sensor position with knowledge of the strip number. For an exact correlation of the projected strips, they may be either color-coded or varied in width sequentially over time in a second step and recorded again. In this so-called gray code method, a correct allocation to the position of the projected surface on the optically structured element is thus determined for each sensor pixel of the camera, and a surface measured point can be determined for each pixel.

To further increase the depth resolution, the strip projection method can be improved by a so-called phase shift method. In this case, the pattern consists of light and dark regions, not of strips with sharp edge transitions; instead the intensity characteristic of this pattern is modulated sinusoidally. The phase position of the projected sine pattern can be determined with a high precision if the phase is shifted in 90° increments, and an image is made of each phase position. The three-dimensional coordinates of the respective surface point can then also be determined from the phase position, which is determined pixel by pixel.

The 3D measured data can be determined by means of a dental handpiece which has optical means for the strip projection method. In addition to these means, the dental handpiece may have a conventional color camera which records color data simultaneously from the same direction. The 3D measured data and the color data may then be compiled to form an image in such a way that the respective color is assigned to each of the measured points of the 3D measured data.

The 3D measured data and color data may also be measured simultaneously by means of a color sensor in a dental handpiece. With this handpiece, the installation of the separate camera is not necessary for the color measurement.

The 3D measured data and the color data may also be measured one after the other in two images. The lighting may also be switched between images. Then the two images are combined on the basis of significant structures or markers in a computer-assisted operation to form an overall image.

In the segmentation method, the first regions with hard tissue and the second regions with soft tissue are identified using the color data. For example, the color of each measured point can be broken down into the hue components of the red-green-blue color space (RGB color space) or the HSV color space. Then each measured point is assigned to one type of tissue using threshold value criteria. When there are high proportions of the red hue component, the measured point may be identified as soft tissue, namely gingiva, and when there are high proportions of the green, blue and red hue components, the measured point may be identified as hard tissue, namely white tooth substance.

To improve the identification of the tissue, the segmentation method may use a color classifier, which is trained with real data to break down the RGB color space and/or the HSV color space into the regions assigned to one type of tissue accordingly. In doing so, certain regions in the color space used are assigned to the respective type of tissue. Regions not assigned to either of the two types of tissue are treated separately in the recording. These regions may be subject to another similar classification in another step to identify the type of tissue with different reflection properties. In this way, it is also possible to identify regions in partial shade or in glossy areas. In the case of a positive identification of a dental restoration or soft tissue, these regions are also used for the recording. In addition, dental accessories such as cotton or dental dams, may also be identified on the basis of their hue to weight them separately in the recording or omit them entirely. This improves the recording.

By weighting the first regions comprising the teeth or dental restoration, and the second regions comprising soft tissue or dental accessories, with different weighting factors, it is possible to improve the quality of the recording, depending on the respective situation. For example, when there is a high proportion of hard tissue in the image, it is advantageous to weight the hard tissue much more than the soft tissue because deformation or movement of the patient's cheek or lips may lead to deformation of the soft tissue and thus to a faulty recording. However, if the proportion of hard tissue in the total image is low, the soft tissue may be weighted much more in order to improve the quality of the recording.

The advantage of the present method is that the weighting, which is adapted to the respective dental situation, improves the quality of the recording.

The first regions may advantageously image tooth substance or a restoration, and the second regions may image gingiva, gingival substitute or dental accessories such as cotton or a dental dam.

The dental restoration may be any restoration part such as a crown, inlay, onlay, veneer or a partial crown. The gingival substitute may have a color similar to that of natural gingiva for aesthetic reasons. Dental accessories may have a wide spectrum of colors. To improve the segmentation method, the dental accessories may preferably be pigmented green or blue so that they can be differentiated better from the surrounding tissue.

A first area section of the first regions of the total area of the image and a second area section of the second regions of the total area of the image may advantageously be calculated in each of the individual images. If the first area section that exceeds a threshold value, only the first regions are taken into account in application of the recording algorithm. If the first area section falls below the threshold value, the first regions are weighted with a first weighting factor, and the second regions are weighted with a second weighting factor, wherein the second weighting factor increases with a decrease in the first area section.

Therefore, the soft tissue is weighted more when a first area section of the hard tissue is smaller. This improves the recording.

The threshold value for the first area section may advantageously be set at a percentage between 5% and 30% of the total area of the image.

Therefore the first regions with hard tissue may be weighted especially strongly in recording above the threshold value, and the second regions with soft tissue may be weighted only slightly or not at all. Below the threshold value, the soft tissue is taken into account to a greater extent. A threshold value between 5% and 30% is advantageous because the weighting of soft tissue yields an improvement in the recording only when the first area section of the hard tissue is small.

The first regions may advantageously be weighted with a first weighting factor of 1.0, and the second regions may be weighted with a second variable weighting factor which is determined for each measured point on the measured surface and decreases when there is an increase in the distance of the measured point from the most proximal first region that images hard tissue.

This is another alternative for the weighting. Due to the increase in the weighting with the increase in the distance from the most proximal first region, this ensures that the soft tissue will be taken into account to a greater extent in the immediate vicinity of the first region. This takes into account the fact that gingiva near a tooth is not as easily deformable as gingiva without nearby tooth substance, and furthermore, there is a low probability that this is a lip or a cheek. The recording is therefore improved in comparison with the aforementioned conventional recording in which only the hard tissue is taken into account.

The second weighting factor may advantageously have a value of 1.0 at the border to the first region and may decline to a minimal value of 0.0 with an increase in the distance from the most proximal first region.

The soft tissue at the border to the hard tissue is thereby taken into account to a greater extent, and the reliability of the recording is increased.

Third regions which cannot be assigned either to the first regions with hard tissue or the second regions with soft tissue may advantageously be identified with the help of threshold value criteria applied to color data. The third regions may be regions that are too bright and occur due to glaring light, or regions that are too dark and occur due to inadequate illumination. A third area section of the total area of the recording is calculated for the third regions.

This third area section represents a quality criterion for the images. If the third area section is too large and exceeds a percentage of 40% for example, the respective image is useless and must be repeated. Only if the third area section is small enough can the respective image be used for the recording. The third regions are not taken into account, and/or they are weighted with a weighting factor of 0.0.

Therefore, defective locations created due to glaring light or inadequate illumination are omitted, thereby improving the recording. The defective regions caused by glaring light or defective illumination will then appear at different locations, depending on the direction of the recording and the incident beam direction in each of the images.

A blur filter may advantageously be applied to the color data in each of the images before segmentation into first regions and second regions.

The image is smoothed in this way and the color segmentation leads to better results in particular at transitions between the first regions and the second regions because these transitions where the differentiation is slight due to electronic noise from the camera appear jagged. This jagged effect is thereby smoothed, so that the calculated transitions between the first regions and the second regions better reflect the actual transitions in the real situation in the patient's mouth.

Each image may advantageously be recorded by using a dental handpiece comprising first means for generating the 3D measured data and second means for generating the color data, wherein the 3D measured data and the color data are detected simultaneously or at a short interval of time from the same direction of recording.

Therefore, both the 3D measured data and the color data can be imaged at the same time by means of the dental handpiece. Then the 3D measured data can be combined with the color data by a computer, and the respective color value can be assigned to each of the measured points in the 3D measured data.

The 3D measured data is advantageously generated using the first means, based on a triangulation method and a strip projection method, and the color data is generated using a conventional color camera.

The dental handpiece therefore comprises both the first means for the strip projection method and the color camera for determining the color data. The 3D measured data and the color data are thus detected simultaneously from the same imaging direction.

The interval of time may advantageously be between 0.2 ms and 100 ms.

The interval of time is therefore short enough to prevent a blur between the image of the 3D measured data and the image of the color data due to the typical jitter when holding the handpiece.

Alternatively, the interval of time may also be more than 100 ms. In this case, the image of the 3D measured data may subsequently be overlaid by the image of the color data with reference to marks or noticeable structures in both images.

BRIEF DESCRIPTION OF THE DRAWINGS

Exemplary embodiments of the invention are depicted in the drawings, which show
FIG. 1 a diagram to illustrate the recording.

EXEMPLARY EMBODIMENTS

Figure 1:
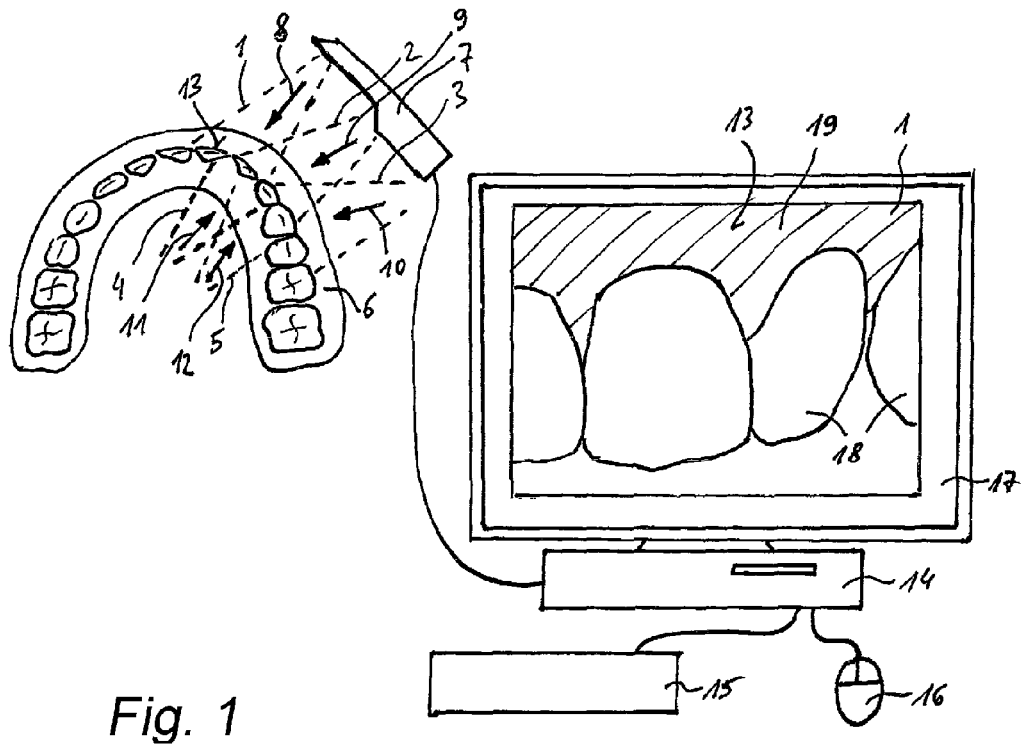

FIG. 1 shows a diagram to illustrate the present method for recording multiple three-dimensional images indicated by dashed lines 1, 2, 3, 4, 5, of a dental object 6, an upper jaw in the present case. The individual images 1, 2, 3, 4 and 5 are recorded by means of the dental handpiece 7 from different imaging directions 8, 9, 10, 11 and 12, which are represented by arrows. The dental handpiece comprises first means for three-dimensional measurement and second means for color measurement. Each of the images thus contains 3D measured data and color data of a measured surface 13 of the object 6 to be recorded. The measured data of each image is transmitted from the dental handpiece 7 to a computer 14 connected to operating means such as a keyboard 15 and a mouse 16, and linked to a display device 17, such as a monitor. In a first step, a blur filter can be applied to the image 1 to smooth the 3D measured data of the measured surface 13. In addition, another blur filter may be applied to the color data to smooth the color data and thus improve the color segmentation. Next, a segmentation process is performed, wherein first regions 18 with hard tissue, namely with tooth substance, are identified, and second regions 19 with soft tissue depicting the gingiva are identified. These two steps are performed for each of the images 1, 2, 3, 4 and 5. Next, the images 1, 2, 3, 4 and 5 are combined to one overall image using the computer-assisted recording algorithm. Matching structures in the images 1, 2, 3, 4 and 5 are recognized by means of a structure recognition algorithm and are superimposed. When employing the recording algorithm, the first region 18 with hard tissue and the second regions 19 with soft tissue are weighted with different weighting factors, pending the respective situation. This improves the quality of the recording.

Figure 2:
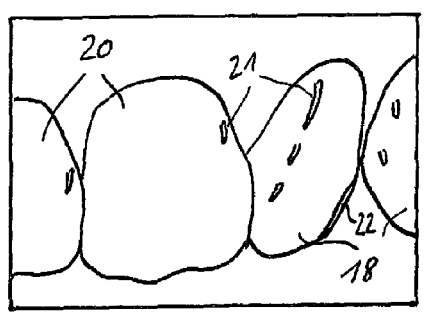
FIG. 2 segmented first regions with hard tissue.

FIG. 2 shows a diagram of the first regions 18 with hard tissue which have been segmented by the use of the segmentation method and depict tooth substance for example. The first regions may also depict a restoration 20 which corresponds in its color to the first tooth substance. Before applying the recording algorithm, regions 21 that are too bright and occur because of glaring light and regions 22 that are too dark and occur due to inadequate illumination are sorted out. This prevents a defective recording because the regions 21 with glare and the regions 22 with shadows depend on the illumination of the dental handpiece 7 and depend on the imaging direction 8, 9, 10, 11 or 12 in each of the images 1, 2, 3, 4 or 5 in different locations.

Figure 3:
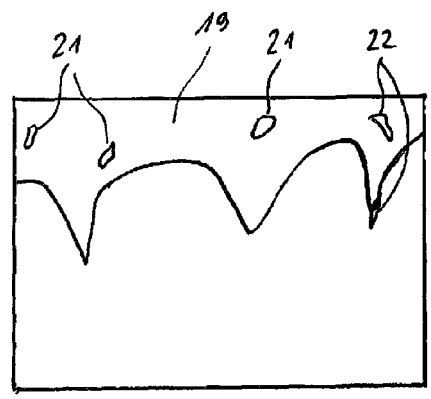
FIG. 3 segmented second regions with soft tissue.

FIG. 3 shows a diagram of the second regions 19 with soft tissue which can depict either true gingiva or gingiva substitute. The second regions 19 were identified using the segmentation method. Before performing the recording, regions 21 which are too bright and occur due to glaring light as well as shadowy regions 22, which occur due to inadequate illumination are sorted out as in FIG. 2. Therefore a defective recording is prevented as explained in conjunction with FIG. 2.

Figure 4:
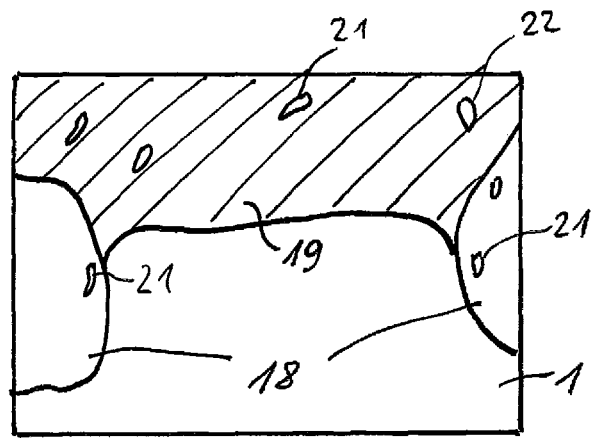
FIG. 4 a diagram of an alternative dental situation.

FIG. 4 shows a diagram of a different dental situation than that in FIG. 1. In FIG. 1, a first area section of the first regions 18 with hard tissue amounts to about 50%. A second area section of the second regions 19 with soft tissue amounts to 30% of the total area of the image 1 in FIG. 1. The remaining third area section of third regions, which cannot be assigned to any of the types of tissue, is about 20%. The first area section is above a fixed threshold value of 30%. In the present dental situation from FIG. 1, the threshold value is therefore exceeded, and therefore the first regions 18 with hard tissue are taken into account with a high weighting when using the recording algorithm. The second regions 19 with soft tissue are taken into account with a low weighting or are omitted entirely.

In the dental situation in FIG. 4, the two middle teeth are missing in comparison with the dental situation in FIG. 1, so that the first area section of the first regions 18 with hard tissue amounts to about 10% of the total area of the image 1, and the second regions 19 with soft tissue amount to about 50% of the total area of the image 1. The remaining third area amounts to about 40%; this accordingly falls below the fixed threshold value of 30% for the first area section of the first regions with hard tissue. Consequently, the first regions are weighted with a first weighting factor and the second regions are weighted with a second weighting factor, such that the second weighting factor increases with a decline in the first area section. For example, the first weighting factor for the first regions 18 may be 1.0, and the second variable weighting factor for the second regions 19 may be 0.5 when the threshold value is exceeded, and up to 1.0 with a decline in the first area quotient. The dependence of the second weighting factor on the area quotient may be defined according to any function such as an exponential function or a linear function.

Figure 5:
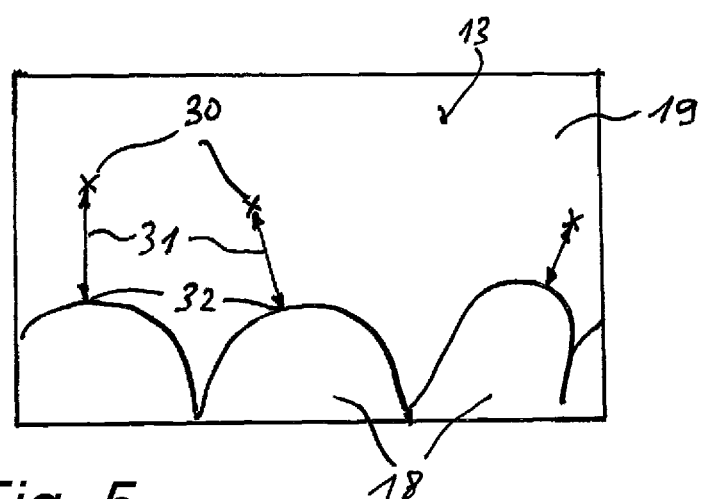
FIG. 5 a diagram to illustrate an alternative weighting.

FIG. 5 shows a diagram to illustrate an alternative weighting of the first regions 18 with hard tissue and the second regions 19 with soft tissue. The first regions 18 in this diagram are weighted with a first fixed weighting factor of 1.0, for example. The second regions 19 are weighted with a variable second weighting factor which is determined for each measured point 30 of the measured surface 13 and decreases as the distance 31 of the respective measured point increases from the most proximal first region 32 with hard tissue. The decline in the second weighting factor as a function of the distance 31 from the most proximal first region 32 may conform to any function such as an exponential function or a linear function. The second weighting factor at the border with the most proximal first region 32 is 1.0 and drops as the distance 31 increases to a value of 0. Thus the soft tissue is weighted just as much as the hard tissue at a small distance from the most proximal region 32 with hard tissue. This method results in an improvement in the recording because the soft tissue which is given greater weight is close to the tooth and thus is more likely to be fixed and immovable.

The invention claimed is:

1. A method of forming an overall image of an object from a plurality of images, the method comprising:
    segmenting each image, of a plurality of images, to identify a first region with hard tissue and a second region with soft tissue, wherein each image includes three-dimensional data and color data, and each image is segmented based on the color data;
    assigning for each image (i) a first weighting factor to the first region and (ii) second weighting factors to points within the second region, respectively,
        wherein a point with a larger distance to a corresponding proximate part of the first region has a smaller second weighting factor than a point with a smaller distance to a corresponding proximate part of the first region; and
    combining the plurality of images to form an overall image based on the first weighting factors and the second weighting factors assigned to the plurality of images.

2. The method according to claim 1, wherein the first regions correspond to tooth substances or dental restorations, and the second regions correspond to gingiva or gingiva substitutes.

3. The method according to claim 1, wherein points in the second region that border the first region are assigned second weighting factors with a value of 1.0, and
    wherein a minimum value for the second weighting factors is 0.

4. The method according to claim 1, further comprising:
    identifying for each image a third region with soft tissue that is not assigned either to the first region or to the second region, the third region being a light region associated with glare or a dark region associated with inadequate illumination,
    wherein the third region is not taken into account in the combining.

5. The method according to claim 1, further comprising:
    applying a blur filter to the color data in each of the plurality of images.

6. The method according to claim 1, further comprising:
    receiving each of the plurality of images from a dental handpiece that generates the three-dimensional data and the color data simultaneously or sequentially from the same imaging direction.

7. The method according to claim 6, wherein the three-dimensional data is generated using a triangulation method and a strip projection method, and the color data is generated using a color camera.

8. The method according to claim 6, wherein the three-dimensional data and the color data are generated sequentially within an interval of time that is between 0.2 ms and 100 ms.

9. An apparatus for forming an overall image of an object, comprising:
    a computer configured to:
        segment each image, of a plurality of images, to identify a first region with hard tissue and a second region with soft tissue, wherein each image includes three-dimensional data and color data, and each image is segmented based on the color data,
        assign for each image (i) a first weighting factor to the first region and (ii) second weighting factors to points within the second region, respectively,
            wherein a point with a larger distance to a corresponding proximate part of the first region has a smaller second weighting factor than a point with a smaller distance to a corresponding proximate part of the first region, and
        combine the plurality of images to form an overall image based on the first weighting factors and the second weighting factors assigned to the plurality of images.

10. The apparatus according to claim 9, wherein the first regions of the plurality of images correspond to tooth substances or dental restorations, and the second regions of the plurality of images correspond to gingiva or gingiva substitutes.

11. The apparatus according to claim 9,
    wherein points in the second region that border the first region are assigned second weighting factors with a value of 1.0, and
    wherein a minimum value for the second weighting factors is 0.

12. The apparatus according to claim 9, wherein the computer is further configured to:
    identify for each image a third region with soft tissue that is not assigned either to the first region or to the second region, the third region being a light region associated with glare or a dark region associated with inadequate illumination,
    wherein the third region is not taken into account when the plurality of images are combined.

13. The apparatus according to claim 9, wherein the computer is further configured to:
    apply a blur filter to the color data in each of the plurality of images.

14. The apparatus according to claim 9, wherein the computer is further configured to:
    receive each of the plurality of images from a dental handpiece that generates the three-dimensional data and the color data simultaneously or sequentially from the same imaging direction.

15. The apparatus according to claim 14, wherein the three-dimensional data is generated using a triangulation method and a strip projection method, and the color data is generated using a color camera.

16. The apparatus according to claim 14, wherein the three-dimensional data and the color data are generated sequentially within an interval of time that is between 0.2 ms and 100 ms.

17. A method of forming an overall image of an object from a plurality of images, the method comprising:
    segmenting each image, of a plurality of images, to identify a first region with hard tissue and a second region with soft tissue, wherein each image includes three-dimensional data and color data, and each image is segmented based on the color data;
    calculating (i) a first area section for each image that represents a percentage of a total area of the image identified as the first region, and (ii) a second area section for each image that represents a percentage of a total area of the image identified as the second region;
    comparing the first area section for each image to a predetermined threshold,
        wherein if an image has a first area section that is greater than a predetermined threshold, then a first weighting factor is assigned to the first area section and a second weighting factor is assigned to the second region,
        wherein if an image has a first area section that is less than a predetermined threshold, then a first weighting factor is assigned to the first area section and a second variable weighting factor is assigned to the second region, and
        wherein a value of the second variable weighting factor depends on a value of the first area section; and
    combining the plurality of images to form an overall image based on the first and second weighting factors assigned to the plurality of images.

18. The method according to claim 17, wherein the value of the second variable weighting factor increases as the value of the first area section decreases.

19. The method according to claim 18, wherein the dependence of the value of the second variable weighting factor on the first area section is expressed by an exponential function.

20. The method according to claim 18, wherein the dependence of the value of the second variable weighting factor on the first area section is expressed by a linear function.

21. An apparatus, comprising:
    a computer configured to:
        segment each image, of a plurality of images, to identify a first region with hard tissue and a second region with soft tissue, wherein each image includes three-dimensional data and color data, and each image is segmented based on the color data for the image;
        calculate (i) a first area section for each image that represents a percentage of a total area of the image identified as the first region, and (ii) a second area section for each image that represents a percentage of a total area of the image identified as the second region;
        compare the first area section for each image to a predetermined threshold,
            wherein if an image has a first area section that is greater than a predetermined threshold, then a first weighting factor is assigned to the first area section and a second weighting factor is assigned to the second region,
            wherein if an image has a first area section that is less than a predetermined threshold, then a first weighting factor is assigned to the first area section and a second variable weighting factor is assigned to the second region, and
            wherein a value of the second variable weighting factor depends on a value of the first area section; and
        combine the plurality of images to form an overall image based on the first and second weighting factors assigned to the plurality of images.

22. The apparatus according to claim 21, wherein the value of the second variable weighting factor increases as the value of the first area section decreases.

23. The apparatus according to claim 22, wherein the dependence of the value of the second variable weighting factor on the first area section is expressed by an exponential function.

24. The method according to claim 22, wherein the dependence of the value of the second variable weighting factor on the first area section is expressed by a linear function.

* * * * *